US008333697B2

(12) United States Patent
McKay et al.

(10) Patent No.: US 8,333,697 B2
(45) Date of Patent: Dec. 18, 2012

(54) DIAGNOSTIC KITS AND METHODS FOR DIAGNOSIS OF AXIAL PAIN WITH OR WITHOUT RADICULOPATHY

(75) Inventors: William F. McKay, Memphis, TN (US); Jeffrey M. Gross, Memphis, TN (US); Hai Trieu, Cordova, TN (US); Josee Roy, Germantown, TN (US); Susan J. Drapeau, Cordova, TN (US); Michael J. Schendel, Andover, MN (US); Andrew J. Lowenthal Walsh, St. Paul, MN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1146 days.

(21) Appl. No.: 11/449,464

(22) Filed: Jun. 8, 2006

(65) Prior Publication Data
US 2007/0298407 A1 Dec. 27, 2007

(51) Int. Cl.
*A61B 5/00* (2006.01)
*A61K 51/00* (2006.01)
(52) U.S. Cl. ........... 600/309; 424/1.65
(58) Field of Classification Search .......... 623/10; 600/309; 424/1.65
See application file for complete search history.

(56) References Cited

U.S. PATENT DOCUMENTS

| | | | |
|---|---|---|---|
| 6,229,024 B1* | 5/2001 | Schmued | 549/391 |
| 6,289,229 B1* | 9/2001 | Crowley | 600/310 |
| 6,541,265 B2* | 4/2003 | Leeuwenburgh | 436/86 |
| 6,764,831 B2 | 7/2004 | Cameron, Sr. et al. | |
| 7,235,366 B1* | 6/2007 | Bell et al. | 435/7.1 |
| 2004/0121343 A1* | 6/2004 | Buechler et al. | 435/6 |
| 2005/0158719 A1* | 7/2005 | Sato et al. | 435/6 |
| 2006/0009478 A1 | 1/2006 | Friedmann et al. | |
| 2007/0060618 A1* | 3/2007 | Cosford et al. | 514/332 |
| 2007/0148092 A1* | 6/2007 | Biswal et al. | 424/1.69 |

OTHER PUBLICATIONS

Sawynok, "Topical and Peripherally Acting Analgesics.", *Pharmacological Reviews*, 55(1), (2003), 1-20.
Cameron, et al., "A Prospective Study of Serum Pseudocholinesterase Levels in Patients With Chronic Spinal Pain.", *Spine*, 25(15), (2000), 1917-1924.

* cited by examiner

*Primary Examiner* — Kevin T Truong
*Assistant Examiner* — David Bates

(57) ABSTRACT

The invention provides kits developed to analyze ex vivo, a sample retrieved from the area of the pathological condition for diagnosis and monitoring the pain generator(s) of axial pain with or without radiculopathy and methods for screening therapeutic compounds potentially useful for treating axial pain with or without radiculopathy. Alternatively, degenerated discs can be monitored and treated before occurrence of a pathological pain condition. Pain markers and markers of degenerating disc include markers of neuronal, vascular, immune and matrix elements.

21 Claims, 1 Drawing Sheet

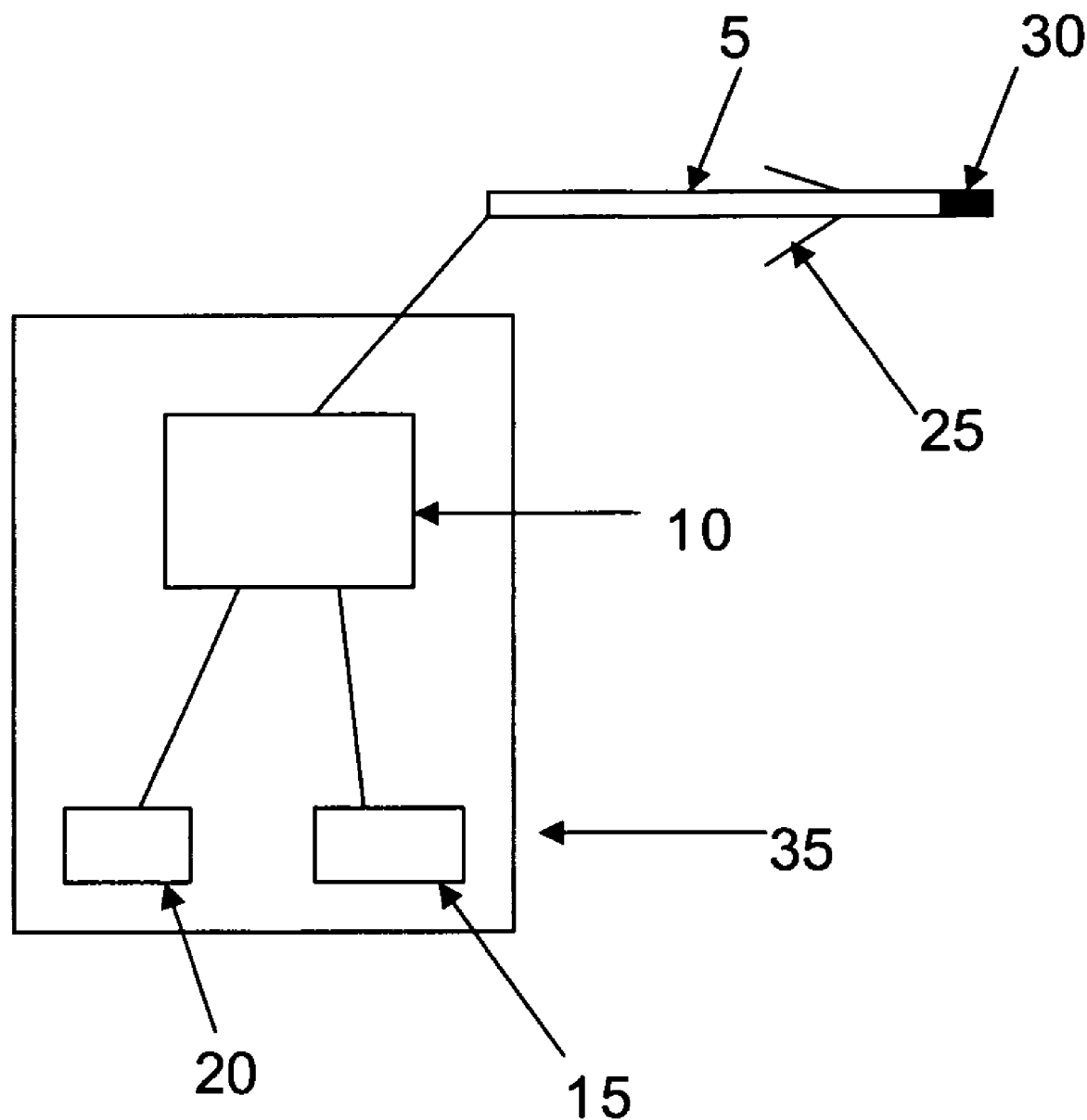

DIAGNOSTIC KITS AND METHODS FOR DIAGNOSIS OF AXIAL PAIN WITH OR WITHOUT RADICULOPATHY

FIELD OF THE INVENTION

This invention relates to diagnostic kits and methods useful for diagnosis and monitoring the pain generator(s) of axial pain with or without radiculopathy and methods for screening test compounds potentially useful for treating axial pain with or without radiculopathy.

BACKGROUND

The spine is a remarkably strong and flexible structure that is capable of withstanding substantial forces. A spine is formed from a plurality of vertebrae, each of which is individually separated from the other by a disc. The discs are anterior to the spinal cord, which runs through the spinal canal of the vertebrae. The discs have several functions, one of which includes serving as shock absorbers for the vertebrae.

Each disc has a relatively tough outer layer called the annulus fibrosus that surrounds a gel-like inner layer called the nucleus pulposus. The annulus fibrosis is composed of concentric layers of intertwined annular bands, which are arranged to resist forces placed upon the spine. The cartilaginous endplate separates the nucleus pulposus and annulus fibrosus from the adjacent vertebrae. The posterior longitudinal ligament strongly attaches to the annulus fibrosus. The nucleus pulposus is composed of cells from the primitive notochord in childhood and chondrocyte-like cells in adulthood, and contains significant amounts of substances capable of exciting, or increasing the excitability of, sensory nerves. These substances include prostaglandin E, histamine-like substances, potassium ions, lactic acid, and several polypeptide amines.

Pain arising from the disc or elements adjacent to an intervertebral disc may cause axial pain also called discogenic pain with or without a radiculopathy component. Generally, though not always, to experience pain in a particular region the presence of nerve endings in that region is required. One source of pain is caused by the activation of specific nociceptors connected with C- and A-delta fibers. Another source of pain involves injury to sensory fibers, or damage to the central nervous system. Alternatively, abnormal interactions between neuronal extensions of sensory and autonomic nature can also be involved in symptomatic pain. Hence, the innervation of the disc and elements adjacent to an intervertebral disc is of interest to the study of discogenic pain.

Neuronal extensions innervating the disc and region adjacent to the disc are of motor, sensory or autonomic nature. Normal discs are rarely innervated deeper than the outer third of the annulus fibrosus. However, there are indications that degenerating or problematic discs have nerve extensions that extend centripetally beyond the outer third of the annulus fibrosis, reaching as far as the inner third of the annulus fibrosis, or even into the nucleus pulposus. The invasion of such neuronal extensions may be a source of pain, particularly if they come into contact with those substances in the nucleus pulposus that are capable of exciting such neuronal extensions. Signs of degeneration associated with the development of axial pain with or without radiculopathy such as increasing innervation have also been found in elements adjacent to the disc, for example the endplates.

Discs are generally avascular, with the transport of nutrients and metabolites occurring primarily through diffusion. However, degenerations tend to be more vascular than normal discs. This centripetally invasive vascularization of the disc, analogous to the neuronal invasion, may contain a perivascular nerve network with vasomotor or vasosensory functionalities. Further, increased vascularization of the disc is associated with increased innervation, and hence increased chances for discogenic pain.

A degenerating disc can be a contained disc or a herniated disc and cause discogenic pain also referred to as axial pain with or without radiculopathy. Herniation could be of a contained nature, for example, bulging of the disc. A herniated disc can also be ruptured with release of discal elements, such as the nucleus pulposus, outside the disc. A degenerating disc can affect the surrounding neuronal elements including the spinal nerve roots and cause radicular pain or radiculopathy. Radiculopathy also referred to sciatica or arm or leg pain depending on the level of the spine affected by the degeneration.

Changes in the appearance of the degenerating disc and/or elements adjacent to the disc can be associated with changes in matrix components including changes in density such as increased density of the nucleus pulposus, level and type of extracellular matrix components such as proteoglycans, metalloproteinases and proteolytic enzymes, collagen and fibronectin fragments and content in nitric oxide and free radicals.

Immune elements including pro-inflammatory agents including cytokines, chemokines, growth factors, peptides, polypeptides and nitric oxide synthetase can also be involved in the degenerative process and development of symptomatic pain associated with axial pain with or without radiculopathy clinical conditions.

In a Gallup Survey, 42% of American adults said that they experienced pain on a daily basis. Amongst such sufferers of chronic pain, spine-related problems constitute the bulk of the complaints. Back and leg pain has been estimated to exist in as much as 66% of the general population. Beyond the substantial discomfort that back and leg pain inflicts upon individuals, spine-related pain also incurs heavy social costs. For example, as many as one million spine surgeries, and as many as five million interventional procedures, are estimated to be performed in the United States each year. Well beyond the purely medical and psychological burdens of such procedures, the subsequent social costs related to productivity, disability compensation, and lost taxes, are substantial.

Accordingly, better strategies to diagnose the precise location of the pain generator(s) involved in axial pain conditions with or without radiculopathy are needed in order to increase the effectiveness of therapeutic interventions.

In addition, better strategies to monitor the progression of pathological changes in the disc or adjacent to an intervertebral disc are needed to enable prophylactic treatment before the development of a painful condition.

SUMMARY OF THE INVENTION

The current invention fulfills this and other foregoing needs by providing devices, methods, and compositions useful for diagnosis and monitoring the pain generator(s) and markers of degeneration involved in axial pain conditions with or without radiculopathy and methods for screening therapeutic compounds potentially useful for treating these conditions.

In one aspect, the invention provides a device for diagnosing and monitoring the pain generator(s) and marker(s) of degeneration involved in axial pain conditions with or without radiculopathy, comprising a detector for measuring an amount of a pain marker or a marker of disc degeneration, the detector comprising a sensing area, wherein the sensing area is at least partially insertable inside of or adjacent to an intervertebral disc. In another embodiment, the device further comprises a processor, operably connected to the detector and a display operably connected to the processor.

In another aspect, the invention provides a method of diagnosing and monitoring the pain generator(s) and marker(s) or degeneration involved in axial pain conditions with or without radiculopathy, in a patient comprising determining an amount of a pain marker or a marker of degeneration, in a location inside of or adjacent to an intervertebral disc; comparing the amount of the pain marker or marker of degeneration, from the patient with the normal range of the marker in a corresponding location, wherein the amount of the pain marker or marker of degeneration, outside of the normal range indicates a current or a potential pain generator. In one embodiment, the amount of pain marker or marker of degeneration, is evaluated by using a device that includes a detector. In another embodiment, the amount of pain marker or marker of degeneration, is evaluated by imaging techniques including radiography, MRI, PET or SPECT, CT, fluoroscopy, luminescence and any combination thereof. In another embodiment, the amount of a pain marker or marker of degeneration is measured in a sample retrieved from the disc or from elements adjacent to the disc and analyzed ex vivo.

In different embodiments of the invention, the pain marker or marker of disc degeneration comprises a compound selected from the group consisting of markers of neuronal, immune, vascular and matrix elements, and any combination thereof.

More particularly, the pain marker or marker of degeneration can be a marker of neuronal element and selected from the group consisting of neurotoxins, for example, a dye, neuronal growth factors including nerve growth factor, brain-derived growth factor, glial-derived growth factor, neurotrophin-3, neurotrophin-4, insulin-growth factor, fibroblast growth factor and leukemia inhibitory factor, extra-cellular matrix components including chondroitin sulfate proteglycans, netrins, semaphorins and myelin/oligodendrocyte growth inhibitors, such as Nogo, MAG and Omgp, cell adhesion molecules, such as NCAM, N-cadherins and integrins, a cytoskeletal element of the growth cone or neurofilaments, agents that can desensitize neuronal elements such as camphor, menthol, piperine, mustard oil, curcumin and eugenol and vanilloid receptor agonists and antagonists such as 8-Methyl-N-vanillyl-trans-6-nonenamide (Capsaicin); Z-Capsaicin; Gingerol; Zingerone; 8-Methyl-N-vanillylnonanamide (Dihydrocapsaicin); 6,7-Deepoxy-6,7-didehydro-5-deoxy-21-dephenyl-21-(phenylmethyl)-daphnetoxin, 20-(4-hydroxy-5-iodo-3-methoxybenzeneacetate) (5'-Iodoresiniferatoxin); (+)-Isovelleral; N-Vannilyloleoylamide (Olvanil); Phorbol 12,13-dinonanoate 20-homovanillate; Resiniferatoxin; N-(3-Methoxyphenyl)-4-chlorocinnamide (SB-366791); 2,3,4-Trihydroxy-6-methyl-5-[(2E, 6E)-3,7,11-trimethyl-2,6,10-dodecatrienyl]benzaldehyde (Scutigeral); 6,7-Deepoxy-6,7-didehydro-5-deoxy-21-dephenyl-21-(phenylmethyl)-20-(4-hydroxybenzeneacetate)daphnetoxin (Tinyatoxin); capsaicin synthetics; and capsaicin derivatives and vanilloid receptor antagonist such as N-[2-(4-Chlorophenyl)ethyl]-1,3,4,5-tetrahydro-7,8-dihydroxy-2H-2-benzazepine-2-carbothioamide (Capsazepine); [N-(4-Hydroxy-3-methoxyphenyl)methyl]-5Z,8Z,11Z,14Z-eicosatetraenamide] (Arvanil); N-(3-Methoxyphenyl)-4-chlorocinnamide (SB-366791) and 5'-iodoresiniferatoxin, agents that can reveal the presence and levels of neuronal receptors and related ligands and molecules involved in trafficking, breakdown and recycling of the ligands and receptors including nociceptors, adrenergic, cholinergic, glutamate, GABA, serotonine, somatostatin opioids, ATP, $Na^+$, $K^{+Ca2+}$, cannabinoids, Substance P and neuropeptide receptors such exemplary agents may include acetylcholine, acetylcholinesterase glutamate, adrenaline, epinephrine, botulinum toxin, anti-convulsants, anesthetics, analgesics, opioids and cannabinoids, agents that can detect neuronal supporting cells or glial cells including astrocyte, oligodendrocyte, microglia and Schawnn cells markers such as Glial Fibrillary Acidic Protein, S-100, CR3 receptor and glial toxins such as fluorocitrate and any combinations thereof.

In different embodiments of the invention, the pain marker or marker of degeneration is an marker of immune element and selected from the group consisting of inflammation-linked cytokines, chemokines, potassium ions, lactic acid, neuropeptides and several polypeptide amines, bradykinin, histamine, prostaglandins ligands and related receptors and molecules involved in trafficking, breakdown and recycling of ligands and receptors including, without limitation IL-1, IL-6, IL-8, IL-10, TNF-alpha, INF and IFN regulatory factor 3, nitric oxide synthetase, Toll-like receptor and adaptor molecules and agents that can interact with immune elements such as steroids, nonsteroidal anti-inflammatory drugs, COX inhibitors, NFkB modulators and any combinations thereof.

In different embodiments of the invention, the pain marker or marker of degeneration is a marker of vascular element and selected from the group consisting of angiogenic and antiangiogenic ligands and related receptors and molecules involved in trafficking, breakdown and recycling of ligands and receptors including anti-angiogenic steroid or an angiostatic steroid, such as anecortave acetate or triamcinolone acetonide, growth factor or cytokine such as vascular growth factor, fibroblast-growth factor, angiopoietins, pigment epithelium-derived factor or α-IFN, vascular extra-cellular matrix components including Matrix metalloproteinase and modulators including marimastat, a vascular cell adhesion molecule such as a cadherin or integrin, marker of vascular elements such as Von Willebrand factor and any combinations thereof.

In different embodiments of the invention, the pain marker or marker of degeneration is a marker of matrix element including tissue density of, for example, the normally gel-like nucleus pulposus, level and type of extracellular matrix components such as proteoglycans, metalloproteinases and proteolytic enzymes, keratin sulfate, collagen, fibronectin fragments, free radicals, nitric oxide, and any combinations thereof.

In other embodiments of the invention, the pain marker or marker of degeneration may comprise a physical activity or a physical stimulus, such as, for example, pressure, neuronal electrical activity, thermal changes, pH, water content, tissue density, absorption of electromagnetic radiation, and any combination thereof.

In other embodiments of the invention, the pain marker or marker of degeneration is a neuronal, immune, vascular or marker of matrix element that has been modified so it can be used with imaging techniques including radiography, MRI, PET or SPECT, CT, fluoroscopy, luminescence and any combination thereof. More specifically, neuronal, immune, vascular or marker of matrix element can be linked to a radioisotope, such as, for example, $^{18}F$, $^{3}H$, $^{124}I$, $^{125}I$, $^{131}I$, $^{35}S$, $^{14}C$, $^{11}C$ or a fluorescent molecule. Exemplary agents include modified agents that can bind opioid receptors such as $^{18}F$ 1-(3-fluoropropyl)-4-(4-cyanophenoxymethyl)piperidine or [(18)F]FPS or $^{18}F$-FPS, $^{3}H$ and $^{11}C$ carfentanil, $^{3}H$ pentazocine, $^{3}H$-1,3 di-ortho-tolylguanidine, (+)-p-$^{11}C$ methylvesamicol, $^{11}$C SA4503, $^{11}$C SA5845, N-[$^{18}$F]4'-fluorobenzylpiperidin-4yl-(2-fluorophenyl)acetamide ([18F]FBFPA), 3-(4-chlorobenzyl)-8-[$^{11}$C]methoxy-1,2,3,4-tetrahydrochromeno [3,4-c]pyridin-5-one, $^{11}$C nemonapride, radiolabeled pentazocine, progesterone, SKF10,047, DuP734, BD1008, SM-21, haloperidol, DTG, progesterone, modified agents that can bind glutamate receptor $^{3}$H MK801, 1-amino-3-[$^{18}$F] fluoromethyl-5-methyl-adamantane, $^{11}$C-ABP688, modified agents that can detect cholinergic receptor and transmission such as [$^{18}$F]fluoroethoxy-benzovesamicol, 2-[$^{18}$F]F-A-85380, [$^{11}$C]-mecamylamine, 5-(3'-fluoropropyl)-3-(2-(S)-pyrrolidinylmethoxy)pyridine (nifrolidine), 5-(2-(4-pyridinyl)vinyl)-6-chloro-3-(1-methyl-2-(S)-pyrrolidinylmethoxy)pyridine, [N-$^{11}$C-methyl]-benztropine neuronal glial marker such as molecules that can bind to the peripheral benzodiazepine receptor including $^{11}$C-R-PK11195, a radiolabeled antibody such as a radiolabeled antibody that can bind the marker of matrix element, keratin sulfate.

In another aspect, the invention provides a method of testing an ability of a treatment comprising administering a therapeutic compound to reduce the intensity of the signal derived from the pain marker of marker of degeneration, the method comprising: determining an amount of a pain marker or marker of degeneration in a location inside of or adjacent to an intervertebral disc at a first time, said first time is prior to a first administration of the therapeutic compound; determining an amount of the pain marker or marker of degeneration in the location inside of or adjacent to the intervertebral disc at a second, later time; whereby $|M_1-N|>|M_2-N|$ indicates that the treatment is efficient in reducing axial pain with or without radiculopathy or the likelihood thereof in the future, wherein $M_1$ equals to the amount of the pain marker measured at the first time; $M_2$ equals to the amount of the pain marker or marker of degeneration measured at the second time; and N equals to the normal range or amount of the pain marker or marker of degeneration. In different embodiments of the invention, the treatment comprises the identity of the therapeutic compound, the combination of the therapeutic compounds, the dosage of the therapeutic compounds, and other variables of treatment.

In yet another aspect, the invention provides a method of monitoring axial pain with or without radiculopathy or a likelihood thereof in a future, comprising: determining an amount of a pain marker or marker of degeneration in a location inside of or adjacent to an intervertebral disc at a first time; determining an amount of the pain marker or marker of degeneration in the location inside of or adjacent to the intervertebral disc at a second, later time; whereby $|M_1-N|<|M_2-N|$ indicates that axial pain with or without radiculopathy or the likelihood thereof in the future has increased, and $|M_1-N|>|M_2-N|$ indicates that pain or the likelihood thereof in the future has decreased, wherein $M_1$ equals to the amount of the pain marker or marker of degeneration measured at the first time; $M_2$ equals to the amount of the pain marker measured at the second time; and N equals to the normal range or amount of the pain marker or marker of degeneration.

In another aspect, the invention provides a provocative test aiming at increasing, directly or indirectly, the signal derived from the pain marker or marker of degeneration in order to improve the sensitivity of the detection method comprising: administration of the pain marker or marker of degeneration, administration of an activator followed by the detection process. Alternatively, the activator can be administered prior or concurrently to the pain marker or marker of the degeneration. The activator could be of a chemical, biological or physical nature.

BRIEF DESCRIPTION OF THE FIGURES

FIG. 1 illustrates one embodiment of a device of the present invention.

DETAILED DESCRIPTION

The present invention provides devices, methods, and compositions useful for diagnosis and monitoring of discogenic pain and methods for screening therapeutic compounds potentially useful for treating axial pain with or without radiculopathy.

Definitions

To aid in the understanding of the invention, the following non-limiting definitions are provided:

The term "adjacent to" the disc means a location within the spinal column.

The term "spinal column" includes neuronal, bony, vascular and soft tissue components. This includes the vertebral bodies and all their associated joints (facets, costovertebral joints, and disc interfaces), the intervertebral discs, the intrinsic musculature, the spinal cord, spinal nerves, sympathetic nerves and ganglia associated with the axial skeleton, vertebral and disc innervations, and all associated blood vessels.

The term "axial" refers to the head, neck and/or back of a subject.

The term "diagnostic" or "diagnosing" means identifying the presence, absence, and location of one or more pain generators or potential pain generators associated with axial pain with or without radiculopathy.

The term "disc" may be any disc within a spinal column, including cervical, thoracic and lumbar discs.

The term "disc region" is intended to include a region extending about 5 cm from the surface of a disc, the surface of the disc, as well as interior regions within the disc.

The term "degeneration" refers to anatomical signs of degeneration, which can include changes in the height of the disc, the level of hydration of the disc, ruptured or contained herniation, annular bulging, the presence of tearing or osteophytes. A reduction in the height of the disc may be one of the most common, early and easily detectable changes present in a degenerating disc. Another sign of degeneration is normally loss of the T2 weighted signal on an MRI scan; this is indicative of a loss of hydration of the nuclear tissue. The degeneration can be a contained disc that occupies the space determined by the size of the endplates or a herniated disc. Herniation could be of a contained nature called, for example, bulging of the disc or a herniated disc can also be ruptured with release of discal elements, such as the nucleus pulposus, outside the disc. Signs of degeneration such as inflammation, tissue density, changes in pH, increased innervation and vascularization can also be found in elements adjacent to the disc.

The term "radiculopathy" refers to radicular leg or arm pain derived from abnormalities of the disc or elements adjacent to the disc that can affect a spinal root or other neuronal elements within the spinal column.

The term "degeneration" refers to a traumatic or progressive abnormality linked to the development of an axial pain with and without radiculopathy condition. Suitable non-limiting examples of degeneration in the intervertebral disc or the area adjacent to the disc include bulging or protrusion, inflammation, pressure, changes in neuronal, vascular, immune or matrix elements, electrical activity, water content, tissue density, and pH.

The term "fragments" of a protein should be interpreted broadly and should include the whole protein.

The term "inflammation-linked cytokines" refers to both pro-inflammatory cytokines, such as, for example, TNF-alpha, IL-1 and IL-8, and anti-inflammatory cytokines, such as, for example, IL-4 and IL-10. In some situations, it may be more advantageous to quantify pro-inflammatory cytokines as they appear when an inflammation occurs locally and disappear quickly when the inflammation subsides. On the other hand, anti-inflammatory cytokines may be detected even after the inflammation has subsides. Igarashi et al., *SPINE* 29(19): 2091-2095 (2004).

The term "neuronal element" includes a neuron body; extensions of a neuron, such as axons, axonal branches, dendrites or growth cones; and supporting cells, such as glial cells including astrocytes, Schwann cells microglia and oligodendrocytes.

The term "vascular element" includes blood vessels, capillaries and endothelial cells.

The term "matrix element" refer to elements within the disc or adjacent to the disc that are not neuronal, vascular or immune elements.

The term "marker" refers to a chemical, biological or physical agent that can, directly or indirectly, reveal the presence, the amount or activity of a neuronal, vascular, immune or matrix element within the pain generator(s) or potential pain generator(s) associated with the development of axial pain with or without radiculopathy conditions.

The term "marker of degeneration" refers to a marker that can identify a potential pain generator within the disc or an element adjacent to the disc that is associated with the development of future painful conditions.

The term "pain marker" refers to a marker that can identify a pain generator within the disc or an element adjacent to the disc and associated with painful conditions.

The term "pain generator(s)" refers to the disc or elements adjacent to the disc identified as key element(s) involved in painful conditions and revealed by pain markers.

The term "potential pain generator(s)" refers to disc or elements adjacent to the disc identified as key element(s) involved in conditions that may potentially become painful and revealed by markers of degeneration.

The term "activator" refers to a chemical, biological or physical agent that can reveal, directly or indirectly, the presence of or improve the signal derived from a pain marker or marker of degeneration within pain generator(s) or potential pain generator(s) associated with development of axial pain with or without radiculopathy conditions.

The term "therapeutic compound" refers to a chemical, biological or physical agent that can modulate a pain marker or marker of degeneration.

The term "modulate" refers to reducing the activity, concentration, number of or level of a marker or neuronal, vascular, immune or matrix element.

The term "patient" includes a living organism belonging to the phylum Chordata upon which the methods and/or devices of the current invention is used. The term includes, without limitation, humans.

The term "practitioner" means a person who is using the methods and/or devices of the current disclosure on the patient. This term includes, without limitation, doctors, other medical personnel, veterinarians, and scientists.

The terms "quantifying," "determining quantity," "determining an amount," or determining a number" of a parameter includes determining both absolute values (e.g., meters, grams, moles) and relative values (e.g., relative light units or ratios compared to control values). This can also be estimated or calculated values, wherein the level of one item is estimated or calculated based on a measured value.

The term "treating" or "treatment" of a disease refers to executing a protocol, which may include administering one or more drugs or physical therapy activities or a surgical procedure to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the patient.

Device

In one aspect, the invention comprises a device for diagnosing axial pain with or without radiculopathy. In one embodiment, depicted in FIG. 1, the device comprises a detector 5 for measuring an amount of a pain marker or marker of degeneration. The detector 5 is operably connected to a processor 10. The processor 10 receives information from the detector 5, analyzes this information, and sends it to a display 15 and, optionally, to an alarm 20.

In one embodiment of the invention, the detector 5 is in a shape of a needle, which, in one embodiment, has a diameter of 18 G or less. The detector 5 at least partially can be inserted in the disc region percutaneously. If desired, the detector 5 may be implanted in a desired location, e.g., in the disc region. It may be advantageous to provide for securing the detector 5 in its target location. Accordingly, in one embodiment, the detector 5 further comprises anchors 25. In the depicted embodiment of the invention two anchors 25 are shown. A person of ordinary skill in the art, however, would recognize that the number of anchors may be more or less than just two. All such modifications are explicitly included in the scope of the current invention. In one embodiment, the detector 5 may be delivered to the target location by a catheter or another insertion device. Preferred materials for the catheter or the insertion device include stainless steel and other rigid compositions. In some embodiments, the insertion device pointed and/or sharp at the tip to facilitate penetration of the skin of the patient.

The detector 5 further comprises a sensing area 30. The sensing area 30 is the part of the detector 5, which has to be placed in the disc region. The sensing area 30 comes into contact with the pain marker or marker of degeneration. Depending on a choice of the pain marker or marker of degeneration, different mechanisms of sensing the amount of the pain marker or marker of degeneration are possible. These mechanisms will be discussed below in connection with a discussion of the pain marker or marker of degeneration.

The processor 10 receives the signals from the detector 5, processes these signals, and sends the processed information to the display 15. Depending on an embodiment of choice, the processor 10 may also be percutaneously inserted or implanted into a patient with the detector 5. In other embodiments, the processor may be located outside of the patient's body. For example, the processor 10 may be located together with the display 15 and, optionally the alarm 20 within a common housing 35, which can be worn, for example, on the patient's wrist or waist.

The display 15 may be an alphanumeric display, showing an absolute or a relative amount of the pain marker. In another embodiment, the display 15 may be a color display changing colors when the amount of the pain marker or marker of degeneration is outside of the pre-determined range, such as, for example, the amount or the range of the pain marker or marker of degeneration in a corresponding location taken from subjects without pain.

Optionally, the device of the present invention may comprise the alarm 20 to alert the patient if the amount of the pain marker or marker of degeneration in a patient is outside of the amount or the range of the pain marker or marker of degeneration in a corresponding location taken from subjects without pain. The alarm 20 may alert the patient by different stimuli or a combination thereof. For example, the alarm 20 may be a light which flashes or changes color. Alternatively, the alarm 20 may emit a sound signal. In another embodiment, the alarm 20 may emit a tactile signal, such as, for example, vibration. In another embodiment, the alarm 20 may emit a light electric shock. In yet another embodiment, the alarm 20 may include a heating or cooling pad which sends a thermal signal to the patient.

A person of ordinary skill will appreciate that the amount of the pain marker or marker of degeneration may be quantified outside of the subject's body. Accordingly, in this embodiment, the sensing area 30 of the detector 5 can be used to collect a sample from the disc region, and the processor 10 and the display 15 are not included in the device. Alternatively, the sensing area 30 may be used for initial reaction with the pain marker or marker of degeneration, such as, for example, substrate enzymatic reaction, antigen-antibody binding or another binding assay and then quantification of the binding or enzymatic activity may be performed ex vivo. The quantification of the pain marker or marker of degeneration could be done visually, or by exposure of the probe to a solution, light source, x-ray source, gas, or other reagent to allow the detection.

In another embodiment, the processor 10 may send information to a device, such as a pump, that provides a treatment to alter directly or indirectly the level of the detected marker or otherwise mitigate pain.

Markers

The instant disclosure describes different markers to diagnose pain and sign of disc degeneration and methods of detection of these markers. A person of ordinary skill in the art will recognize that pain may be diagnosed by quantification of selected chemical or biological compounds, selected physical activities or selected physical stimuli and any combination thereof. The suitable non-limiting examples of physical activities or stimuli are pressure, thermal changes, pH, electrical activity, water content, tissue density, absorption of electromagnetic radiation, and any combination thereof.

This invention describes pain marker or marker of degeneration selected from the group consisting of markers of neuronal, immune, vascular or matrix elements, and any combination thereof.

Suitable examples of marker of neuronal elements include neurotoxins, for example, a dye, neuronal growth factors including nerve growth factor, brain-derived growth factor, glial-derived growth factor, neurotrophin-3, neurotrophin-4, insulin-growth factor, fibroblast growth factor and leukemia inhibitory factor, neuronal extra-cellular matrix components including chondroitin sulfate proteglycans, netrins, semaphorins and myelin/oligodendrocyte growth inhibitors, such as Nogo, MAG and Omgp, neuronal adhesion molecules, such as NCAM, N-cadherins and integrins, a cytoskeletal component of the growth cone and neurofilaments, agents that can interact with neuronal elements including camphor, menthol, piperine, mustard oil, curcumin and eugenol and vanilloid receptor agonists and antagonists such as 8-Methyl-N-vanillyl-trans-6-nonenamide (Capsaicin); Z-Capsaicin; Gingerol; Zingerone; 8-Methyl-N-vanillylnonanamide (Di-hydrocapsaicin); 6,7-Deepoxy-6,7-didehydro-5-deoxy-21-dephenyl-21-(phenylmethyl)-daphnetoxin, 20-(4-hydroxy-5-iodo-3-methoxybenzeneacetate) (5'-Iodoresiniferatoxin); (+)-Isovelleral; N-Vannilyloleoylamide (Olvanil); Phorbol 12,13-dinonanoate 20-homovanillate; Resiniferatoxin; N-(3-Methoxyphenyl)-4-chlorocinnamide (SB-366791); 2,3,4-Trihydroxy-6-methyl-5-[(2E, 6E)-3,7,11-trimethyl-2,6,10-dodecatrienyl]benzaldehyde (Scutigeral); 6,7-Deepoxy-6,7-didehydro-5-deoxy-21-dephenyl-21-(phenylmethyl)-20-(4-hydroxybenzeneacetate) daphnetoxin (Tinyatoxin); capsaicin synthetics; and capsaicin derivatives and vanilloid receptor antagonist such as N-[2-(4-Chlorophenyl)ethyl]-1,3,4,5-tetrahydro-7,8-dihydroxy-2H-2-benzazepine-2-carbothioamide (Capsazepine); [N-(4-Hydroxy-3-methoxyphenyl)methyl]-5Z,8Z,11Z,14Z-eicosatetraenamide] (Arvanil); N-(3-Methoxyphenyl)-4-chlorocinnamide (SB-366791) and 5'-iodoresiniferatoxin, agents that can interact with neuronal ligands and related receptors and molecules involved in trafficking, breakdown and recycling of neuronal ligands and neuronal receptors including nociceptors, adrenergic, cholinergic, glutamate, GABA, serotonine, somatostatin opioids, ATP, $Na^+$, $K^+$, $Ca^{2+}$, cannabinoids, Substance P and neuropeptide receptors including substance P and neuropeptides, acetylcholine, glutamate, GABA, serotonine, somatostatin, adrenaline, epinephrine, botulinum toxin, anti-convulsants, anesthetics, analgesics, opioids and cannabinoids, agents that can detect neuronal supporting cells or glial cells including astrocyte, oligodendrocyte, microglia and Schawnn cells markers such as Glial Fibrillary Acidic Protein, S-100, CR3 receptor and glial toxins such as fluorocitrate and any combinations thereof.

Suitable examples of markers of immune elements of an immune element include inflammation-linked cytokines, chemokines, potassium ions, lactic acid, neuropeptides and several polypeptide amines, bradykinin, histamine, prostaglandins ligands and related receptors and molecules involved in trafficking, breakdown and recycling of ligands and receptors including, without limitation IL-1, IL-6, IL-8, TNF-alpha, INF and IFN regulatory factor 3, Toll-like receptor and adaptor molecules and agents that can interact with immune elements such as steroids, nonsteroidal anti-inflammatory drugs, COX inhibitors, NFkB modulators, nitric oxide synthetase and any combinations thereof.

Suitable examples of marker of vascular elements include angiogenic and antiangiogenic ligands and related receptors and molecules involved in trafficking, breakdown and recycling of ligands and receptors including anti-angiogenic steroid or an angiostatic steroid, such as anecortave acetate or triamcinolone acetonide, growth factor or cytokine such as vascular growth factor, fibroblast-growth factor, angiopoietins, pigment epithelium-derived factor or α-IFN, vascular extra-cellular matrix components including matrix metalloproteinase and modulators including marimastat, a vascular cell adhesion molecule such as a cadherin or integrin, marker of vascular elements such as Von Willebrand factor and any combinations thereof.

Suitable examples of marker of matrix elements include tissue density of the disc or elements adjacent to the disc, for example, the normally gel-like nucleus pulposus, level and type of extracellular matrix components such as proteoglycans, metalloproteinases and proteolytic enzymes, keratin sulfate, collagen, nitric oxide, free radicals, fibronectin fragments, and any combinations thereof.

Suitable examples of markers of neuronal, immune, vascular or matrix elementss that have been modified so they can be used with imaging techniques including radiography, MRI, PET or SPECT, CT, luminescence, include the markers of neuronal, immune, vascular or matrix elements linked to a radioisotope including $^{18}F$, $^3H$, $^{124}I$, $^{125}I$, $^{131}I$, $^{35}S$, $^{14}C$, $^{11}C$ or a fluorescent or luminescent molecules. Suitable examples of radiolabeled markers include modified markers that can bind opioid receptors such as $^{18}$F 1-(3-fluoropropyl)-4-(4-cyanophenoxymethyl)piperidine or [(18)F]FPS or $^{18}$F-FPS, $^3$H and $^{11}$C carfentanil, $^3$H pentazocine, $^3$H-1,3 di-orthotolylguanidine, (+)-p-$^{11}$C methylvesamicol, $^{11}$C SA4503, $^{11}$C SA5845, N-[$^{18}$F]4'-fluorobenzylpiperidin-4yl-(2-fluorophenyl) acetamide ([$^{18}$F]FBFPA), 3-(4-chlorobenzyl)-8-[$^{11}$C]methoxy-1,2,3,4-tetrahydrochromeno[3,4-c]pyridin-5-one, $^{11}$C nemonapride, radiolabeled pentazocine, progesterone, SKF 10,047, DuP 734, BD1008, SM-21 haloperidol, DTG, progesterone, modified markers that can bind to glutamate receptor $^3$H MK801, 1-amino-3-[$^{18}$F]fluoromethyl-5-methyl-adamantane, $^{11}$C-ABP688, modified markers that can detect cholinergic receptor and transmission such as [$^{18}$F]fluoroethoxy-benzovesamicol, 2-[$^{18}$F]F-A-85380, [$^{11}$C]-mecamylamine, 5-(3'-fluoropropyl)-3-(2-(S)-pyrrolidinylmethoxy)pyridine (nifrolidine), 5-(2-(4-pyridinyl)vinyl)-6-chloro-3-(1-methyl-2-(S)-pyrrolidinylmethoxy) pyridine, [N-$^{11}$C-methyl]-benztropine and neuronal glial marker that can bind to the peripheral benzodiazepine receptor including $^{11}$C-R-PK11195, a radiolabeled antibody such as a radiolabeled antibody that can bind the marker of matrix element, keratin sulfate.

In yet another embodiment, the pain marker or marker of degeneration comprises an activator for example a provocative or reactive substance that enables the detection of the neuronal, vascular, immune or marker of matrix element. The activator may be administered separately, prior, concurrently or following administration of the pain marker or marker of degeneration.

Suitable non-limiting examples of activators include agents that can activate neuronal receptors including nociceptors, vanilloid, bradykinin, adrenergic, cholinergic, glutamate, GABA, serotonine, somatostatin opioid, ATP, Na$^+$, K$^+$, Ca$^{2+}$, cannabinoid, Substance P and neuropeptide receptors. Exemplary activators include substance P and neuropeptides, bradykinin, acetylcholine, glutamate, adrenaline, epinephrine, opioid and derivates, capsaicin and derivates, camphor, menthol, piperine, mustard oil, curcumin, eugenol, neurotoxin, activators of blood flow and pro-inflammatory molecules including histamine and pro-inflammatory cytokines.

In other embodiments of the invention, the pain marker or marker of degeneration may comprise an activator of physical nature, such as, for example, pressure, electrical activity, thermal and pH changes, and any combination thereof.

In yet another embodiment, the activator may be administered locally via a catheter positioned at or near the intervertebral disc. In this embodiment, the catheter has a proximal end and a distal end, the proximal end having an opening to deliver the provocative or reactive substance in situ, the distal end being fluidly connected to a pharmaceutical delivery pump. In one embodiment of the invention, the delivery pump is operably connected to a reservoir which may optionally be included in the device of the present invention. The catheter may be positioned via a minimally invasive procedure, such as, for example, by accessing a blood vessel adjacent or supplying blood to the site of the pathological condition.

Pressure.

One of the pain marker or marker of degeneration of this invention is pressure. Use of pressure as the pain marker is especially advantageous if the sensing area 30 of the detector 5 is placed inside the intervertebral disc. There are multiple ways to measure and transmit the information about the amount of pressure from the detector 5 to the processor 10. In one embodiment, the detector can measure the amount of pressure by detecting the strain induced on a sensor element, i.e., transducer. The sensor converts the strain into an electrical signal by measuring the resistance of the strained element, such as is done in piezoresistive-based sensors, or the change in vibrational frequency of that element, such as is done in resonance-based sensors. Pressure-sensitive membranes and circuitry associated therewith is described in details in the U.S. Pat. Nos. 7,007,551 and 6,959,608, entire contents of which are incorporated into the instant disclosure by reference.

Temperature.

Inflammation leading to pain is often accompanied by localized increase in temperature. Thus, detection of temperature increase within the disc region may be used as an marker of immune element or an activator for diagnosis and monitoring of the pain generator(s) and disc degeneration associated with axial pain with or without radiculopathy. Accordingly, in one embodiment, the sensing area 30 comprises a temperature probe.

The design and the methods of making and using a temperature probe, the processing circuits associated therewith are explained in details in multiple patent and non-patent publications, such as, for example, U.S. Pat. No. 6,175,752, which is incorporated herein by reference in its entirety. Briefly, two probe leads are connected to each other by a temperature-dependent element made from a material or a composition with a temperature-dependent characteristic. The probe leads are typically formed using a metal, an alloy, a semimetal, such as graphite, a degenerate or highly doped semiconductor, or a small-band gap semiconductor. Examples of suitable materials include gold, silver, ruthenium oxide, titanium nitride, titanium dioxide, indium doped tin oxide, tin doped indium oxide, or graphite. The temperature-dependent element is typically made using a fine trace of the same conductive material as the probe leads, or another material such as a carbon ink, a carbon fiber, or platinum, which has a temperature-dependent characteristic, such as resistance, that provides a temperature-dependent signal when a voltage source is attached to the two probe leads. The temperature-dependent characteristic of the temperature-dependent element may either increase or decrease with temperature. Preferably, the temperature dependence of the characteristic of the temperature-dependent element is approximately linear with temperature over the expected range of physiological temperatures.

One exemplary method for forming this particular temperature probe includes forming the two spaced-apart channels and then filling them with the metallic or alloyed conductive material. Next, the cross-channel is formed and then filled with the desired material. The material in the cross-channel overlaps with the conductive material in each of the two spaced-apart channels to form an electrical connection.

Proteinaceous Pain Markers.

Another set of pain marker or marker of degeneration utilized in one aspect of this invention are using antibodies directed against a neuronal, vascular, immune and matrix element, for example, antibodies against inflammatory-linked cytokines, neurotransmitters, neuropeptides, growth factors, chemokines, nitric oxide, nitric oxide synthetase, acetylcholine, acetylcholine esterase, bradykinin, histamine, prostaglandins and receptors, cellular adhesion molecules, cytoskeleton elements, extra-cellular matrix components and any combinations thereof. A suitable antibody-based method of detection of chemical substances is described, for example, in the U.S. Pat. No. 7,003,184, which is incorporated herein by reference in its entirety. In this embodiment, the sensing area 30 of the detector 5 comprises an optical fiber, at least one optically responsive detector, such as, for example, FBG sensor, and a coating located adjacent to the optical fiber. In one embodiment of the invention, the coating is located peripherally of the optical fiber. As described in the above-referenced patent publication, the coating is made from a material, which is capable of changing its volume in response to a presence or an amount of the pain marker or marker of degeneration. The change in the volume of the coating alters at least one optical property of the optical fiber. A suitable coating material is a hydrogel. Different types of hydrogels may be used with the current invention. For example, the swelling behavior of polymer gel networks is governed not only by the affinity of polymer chains for solvents, but also by the cross-linking density, (see for example M. Shibayama and T. Tanaka, "Volume phase transitions and related phenomena of polymer gels," in Advances in Polymer Science, vol. 109, Springer Verlag, 1993). The cross-linking density controls the elastic restoring force. Affecting the elastic restoring force in turn affects the equilibrium swelling volume of the gel network.

Polymer gel networks responsive to specific biochemicals can also be prepared by application of stimuli-sensitive complex formation at cross-linking points in the gel network, e.g. application of antigen-antibody binding at cross-linking points.

One way to synthesize such materials is to use the well-known polyacrylamide gel system (PAAm) and including the functionalized recognition molecule in the cross-link-co-polymerization reaction. An example of this is described by T Miyata et al., "A reversibly antigen-responsive hydrogel," Nature, vol. 399, pp. 766-769, 1999, who used the polyacrylamide gel system to conjugate IgG antibody to prepare an antigen-responsive gel. Competitive binding of the free antigen (analyte) break the antigen-antibody (receptor) cross-link, thereby reducing the cross-linking density and triggering a change in gel volume.

Further, the sensor area may comprise a detector housing comprising an area of a porous material. Such design will protect the coating and the optical fiber and at the same time provide an access of the pain marker or marker of degeneration to the coating.

The antibodies to the pain markers, markers of degeneration or fragments thereof can be produced by methods well known to those skilled in the art. For example, monoclonal antibodies to the pain markers can be produced by generation of hybridomas in accordance with known methods. Hybridomas formed in this manner are then screened using standard methods, such as ELISA, to identify one or more hybridomas that produce an antibody that specifically binds to a neuronal, vascular, immune or matrix element or a part thereof.

As an alternative to preparing monoclonal antibody-secreting hybridomas, a monoclonal antibody to the pain markers, markers of degeneration or fragments thereof, may be identified and isolated by screening a recombinant combinatorial immunoglobulin library (e.g., an antibody phage display library) to thereby isolate immunoglobulin library members that bind to the pain markers or fragments thereof. Kits for generating and screening phage display libraries are commercially available from, e.g., Dyax Corp. (Cambridge, Mass.) and Maxim Biotech (South San Francisco, Calif.). Additionally, examples of methods and reagents particularly amenable for use in generating and screening antibody display libraries can be found in the literature.

Polyclonal sera and antibodies may be produced by immunizing a suitable subject, such as a rabbit, with the pain markers, markers of degeneration or fragments thereof (preferably mammalian; more preferably human). The antibody titer in the immunized subject may be monitored over time by standard techniques, such as with ELISA, using immobilized marker protein. If desired, the antibody molecules directed against the pain markers or fragments thereof may be isolated from the subject or culture media and further purified by well-known techniques, such as protein A chromatography, to obtain an IgG fraction, or by affinity chromatography.

Fragments of antibodies to the pain markers, markers of degeneration or fragments thereof may be produced by cleavage of the antibodies in accordance with methods well known in the art. For example, immunologically active F(ab') and F(ab')$_2$ fragments may be generated by treating the antibodies with an enzyme such as pepsin. Additionally, chimeric, humanized, and single-chain antibodies to the pain marker, the marker of degeneration or at least a part thereof, comprising both human and nonhuman portions, may be produced using standard recombinant DNA techniques. Humanized antibodies to the neuronal, vascular, immune or matrix markers or fragments thereof may also be produced using transgenic mice that are incapable of expressing endogenous immunoglobulin heavy and light chain genes, but which can express human heavy and light chain genes.

Acetylcholine.

Electrochemistry is one of suitable methods of detection for neurotransmitters such as catecholamines (e.g., dopamine and epinephrine) and serotonin, as it can be used to determine the low endogenous neurotransmitter concentrations in brain microdialysates and other in vivo samples. Acetylcholine and choline lack an electrophore, so in one embodiment an indirect method is used, based on the products of enzyme reactions.

A suitable non-limiting process of acetylcholine measurement is provided by Bioanalytical Systems (West Lafayette, Ind.). In that process, acetylcholine is first converted to choline by acetylcholinesterase, and choline reacts with choline oxidase to form hydrogen peroxide, which is electrochemically active. Accordingly, in one embodiment, the sensing area 30 comprises a peroxidase enzyme working electrode, which includes sources of acetylcholinesterase and choline oxidase. Using the peroxidase enzyme working electrode for the detection of hydrogen peroxide, basal acetylcholine (in the absence of inhibitors) can be observed, as the wired electrode allows measurement at a potential where background is minimal, thereby lowering the detection limit.

In another embodiment, detection of acetylcholine may be performed through a mechanism similar to the one for detection of the proteinaceous pain markers. In addition to, or instead of, an antibody recognizing acetylcholine, the coating may comprise acetylcholinesterase and choline oxidase. In this embodiment, hydrogen peroxide will create electrical and/or pH change in the coating. Accordingly, a suitable material for the coating on this embodiment of the invention would be a material responding (e.g., swelling) to changes in pH or electrical activities.

Diagnostic Imaging

In another embodiment, the pain markers or markers of degeneration may be directly visualized by labeling the marker of neuronal, immune, vascular or matrix elements with a label. The label may be a radioisotopes or fluorochrome that can be visualized by imaging techniques including radiography, MRI, PET, SPECT, CT or fluoroscopy. For example radioisotope can include $^{18}$F, $^{3}$H, $^{124}$I, $^{125}$I, $^{131}$I, $^{35}$S, $^{14}$C, $^{11}$C. Suitable example of radiolabeled markers of neuronal opioid receptors using $^{18}$F 1-(3-fluoropropyl)-4-(4-cyanophenoxymethyl)piperidine or [(18)F]FPS or $^{18}$F-FPS, $^{3}$H and $^{11}$C carfentanil, $^{3}$H pentazocine, $^{3}$H-1,3 di-orthotolylguanidine, (+)-p-$^{11}$C methylvesamicol, $^{11}$C SA4503, $^{11}$C SA5845, N-[$^{18}$F]4'-fluorobenzylpiperidin-4yl-(2-fluorophenyl) acetamide ([$^{18}$F]FBFPA), 3-(4-chlorobenzyl)-8-[$^{11}$C]methoxy-1,2,3,4-tetrahydrochromeno[3,4-c]pyridin-5-one, $^{11}$C nemonapride, radiolabeled pentazocine, progesterone, SKF 10,047, DuP734, BD1008, SM-21 haloperidol, DTG, progesterone, modified markers that can bind to glutamate receptor $^{3}$H MK801, 1-amino-3-[$^{18}$F]fluoromethyl-5-methyl-adamantane, $^{11}$C-ABP688, radiolabeled markers of neuronal cholinergic receptor and transmission such as [18F]fluoroethoxy-benzovesamicol, 2-[$^{18}$F]F-A-85380, [$^{11}$C]-mecamylamine, 5-(3'-fluoropropyl)-3-(2-(S)-pyrrolidinylmethoxy)pyridine (nifrolidine), 5-(2-(4-pyridinyl)vinyl)-6-chloro-3-(1-methyl-2-(S)-pyrrolidinylmethoxy) pyridine, [N-$^{11}$C-methyl]-benztropine and radiolabeled marker of neuronal glial element such as peripheral benzodiazepine receptor including $^{11}$C-R-PK11195, a radiolabeled antibody such as a radiolabeled antibody that can bind the marker of matrix element, keratin sulfate.

The label may be a radioisotope, such as, for example, $^{18}$F, $^{3}$H, $^{124}$I, $^{125}$I, $^{131}$I, $^{35}$S, and $^{14}$C. These labels may be attached to a marker, for example an antibody, by using a chelating agent, such as EDTA or DTPA, and detected by gamma counter, scintillation counter, PET scanning, or autoradiography. Other methods of labeling the marker are described, for example, in the U.S. Pat. App. No. 2005/0118165 and in Hunter et al., *Nature* 194:495 (1962); G. S. David et al., *Biochemistry* 13:1014-1021 (1974); D. Pain et al., *J Immunol Meth* 40:219-230 (1981); and H. Nygren, *J. Histochem Cytochem.* 30:407 (1982), all of which are incorporated by reference herein.

In other embodiments, the label is a fluorescent label. Common fluorescent labels include fluorescein, dansyl, phycoerythryn, phycocyanin, allophycocyanin, o-phtaldehyde, and fluorescamine. In yet other embodiments, the label may comprise a fluorescence-emitting metal such as, for example, $^{152}$Eu$^{+}$ or other lantanoids. The fluorescence-emitting metals can be attached to the marker, such as, for example, an antibody by using metal-chelating groups such as EDTA or DTPA.

In another embodiment, since radioisotopes may have a limited half-life, labeling of a pain marker or marker of degeneration may be performed within a few hours prior to administration.

A person of ordinary skill in the art will appreciate that the marker, activator and therapeutic agent may be administered to the subject via multiple methods. Among these methods are an intravenous administration, an intramuscular administration, an intrathecal administration, a subcutaneous administration, an epidural administration, an intra-discal administration, a parenteral administration, an oral administration, a direct application onto or adjacent to a site of the pathological condition, and any combinations thereof. A person of ordinary skill in the art will select the appropriate method based on the nature of the pain marker or marker of degeneration.

In yet another embodiment, the marker, the activator and the therapeutic compound may be administered locally via a catheter positioned at or adjacent to the intervertebral disc. In this embodiment, the catheter has a proximal end and a distal end, the proximal end having an opening to deliver the marker in situ, the distal end being fluidly connected to a pharmaceutical delivery pump. In one embodiment of the invention, the delivery pump is operably connected to a reservoir which may optionally be included in the device of the present invention. The catheter may be positioned via a minimally invasive procedure, such as, for example, by accessing a blood vessel adjacent or supplying blood to the site of the pathological condition.

In another embodiment, the activator may be administered in combination with the marker or separately, prior, concurrently or following administration of the pain marker or marker of degeneration.

In another embodiment, the therapeutic agent may be administered in combination with the marker or separately, prior, concurrently or following administration of the pain marker or marker of degeneration.

In yet another embodiment, the labeled marker may be implanted into the subject, for example, in forms of a pump or a depot. A suitable non-limiting design of a depot implant is discussed in details in a co-pending U.S. patent application Ser. No. 11/403,733 entitled Drug Depot Implant Designs And Methods Of Implantation, filed on Apr. 13, 2006. For example, the pump or depot can be implanted to monitor improvement of treated disc or element adjacent to the disc or monitor potential pain generators linked to axial pain with or without radiculopathy.

In another aspect, the invention provides methods for diagnosis of axial pain with or without radiculopathy. In one embodiment, the method comprises determining an amount of a pain marker or marker of degeneration within the disc region. The amount of the pain marker or marker of degeneration can be measured by any method described above. In some embodiments, such as, for example, where the activator is used, and/or where the marker or labeled marker is used, the method may further comprise a step of administering the activator and/or the marker or labeled marker, respectively, and the amount of the pain marker or marker of degeneration (i.e., the test amount) is measured indirectly. The test amount is then compared to a normal amount or range. The test amount outside of the normal amount or range (e.g., the test amount which is significantly different (i.e., p<0.05)) is used to present or potential future pain generator(s) associated with axial pain with or without radiculopathy.

Normal Ranges of the Pain Markers.

Normal ranges of at least some of the pain markers or marker of degeneration have been disclosed previously. For example, it has been shown that intervertebral discs of healthy humans do not express detectable levels of TGF-β1, IL-6, or IL6-R, as measured by immunohistochemistry. Specchia et al., *Eur. Spine J.* 11:145-151 (2002). Accordingly, detection of these markers by the detector 5 will indicate a likelihood of pain or disc degeneration. Another example is the matrix element, keratin sulfate, which is not found in degeneration but not healthy disc in a rat model of disc degeneration. Kairemo K J A et al., J Nucl Med (2001). Levels of other pain markers and markers of degeneration may be obtained from such sources as, for example, fresh cadavers (recently deceased subjects) or healthy volunteers. If the subject is not human, the data on normal values of the pain markers and markers of degeneration may be obtained from lab animals of the same species as the subject.

In yet another aspect, the invention comprises a method of testing an ability of a treatment comprising administering a therapeutic compound to reduce axial pain with or without radiculopathy or a likelihood thereof in a future, the method comprising: determining an amount of a pain marker or marker of degeneration within the disc region at a first time, said first time is prior to a first administration of the therapeutic compound; determining an amount of the pain marker or marker of degeneration within the disc region at a second, later time; whereby $|M_1-N|>|M_2-N|$ indicates that the treatment is efficient in reducing axial pain with or without radiculopathy or the likelihood thereof in the future, wherein $M_1$ equals to the amount of the pain marker or marker of degeneration measured at the first time; $M_2$ equals to the amount of the pain marker or marker of degeneration measured at the second time; and N equals to the normal range or amount of the pain marker or marker of degeneration (i.e., an amount or range from an individual(s) known not to suffer from axial pain with or without radiculopathy).

A person of ordinary skill in the art will recognize that the threshold for pain may vary between different patients. Accordingly, the results of the diagnosing the axial pain, the testing of the potential candidates to relieve the axial pain, and/or the monitoring of the axial pain may be correlated with the pain measurements according to techniques of pain assessment known in the art. Such correlation enable the practitioner to choose the course of treatment which better fits the needs of the patient. The techniques of pain assessment include, without limitation, VAS, Oswestri, and SF-36 Questionnaires. Alternatively, the pain may be assessed based on disc height, disc hydration level, type II collagen level, proteoglycan levels, and any combination of the techniques disclosed above.

In some embodiments, such as, for example, where the activator is used, and/or where marker or labeled marker is used, the method may further comprise a step of administering the activator and/or the marker or labeled marker, respectively, and the amount of the pain marker or marker of degeneration (i.e., the test amount) is measured indirectly.

Another aspect of invention provides multiple kits. In one embodiment, the invention provides a kit comprising a composition for diagnosing a current or potential pain generator of an axial pain condition with or without associated arm or leg radicular pain comprising a pain marker or marker of a degeneration that can be detected by at least one imaging technique, and a set of instructions for efficient and safe use of the kit. In another embodiment, the kit further comprises instructions on how to modify the marker for imaging purposes. In another embodiment, the kit comprises materials necessary to access an amount or an activity of a pain marker or marker of a degeneration from a sample extracted from a disc or an area adjacent to the disc by any method described above. Preferably, the method is selected from the group consisting of an ELISA, an enzymatic reaction, an antibody-antigen assay, and other binding assays where the signal is detected by calorimetric, fluorescence, luminescence or radiometric modalities. In yet another embodiment the kit may provide an activator. A person skilled in the art will undoubtedly appreciate that the set of instruction may be provided in any medium, including, without limitations, printed, audio and video recorded, and electronic.

A person of ordinary skill in the art will undoubtedly understand that "treatment" includes all parameters of alleviating axial pain with or without radiculopathy. Without limitation, such parameters include the identity of the therapeutic compound or a combination of the therapeutic compounds used to alleviate the pain or reduced the signs of degeneration, a dosage of the therapeutic compound or the combination of the therapeutic compound, a frequency of administering the therapeutic compound or the combination of the therapeutic compounds, formulations of the therapeutic compound or the combination of the therapeutic compounds, and a method of administering the therapeutic compound or the combination of the therapeutic compounds.

Since increased neuronal and/or vascular extensions in an intervertebral disc are likely to result in the axial pain with or without radiculopathy, the therapeutic compounds, which can retard the growth of such neuronal and/or vascular extensions, or repel these extensions, thus preventing a formation thereof, or destroy the neuronal and vascular extension already formed in the intervertebral disc, are among the therapeutic compounds which can be tested to ensure the optimal compositions and modes of administration of these therapeutic compounds for treatment of axial pain with or without radiculopathy.

Suitable non-limiting examples of such therapeutic compounds include, without limitation, natural neurotoxins; neurotoxins comprising ammonia or cyanide; bisbenzimide; trypan blue; brilliant blue; methylene blue; indocyanine green; ruthenium red; quinoline yellow; saporin; Rho kinase activators; camphor; menthol; piperine; mustard oil; eugenol; curcumin; 8-Methyl-N-vanillyl-trans-6-nonenamide (Capsaicin); Z-Capsaicin; Gingerol; Zingerone; 8-Methyl-N-vanillylnonanamide (Dihydrocapsaicin); 6,7-Deepoxy-6,7-didehydro-5-deoxy-21-dephenyl-21-(phenylmethyl)-daphnetoxin, 20-(4-hydroxy-5-iodo-3-methoxybenzeneacetate) (5'-Iodoresiniferatoxin); (+)-Isovelleral; N-Vannilyloleoylamide (Olvanil); Phorbol 12,13-dinonanoate 20-homovanillate; Resiniferatoxin; N-(3-Methoxyphenyl)-4-chlorocinnamide (SB-366791); 2,3,4-Trihydroxy-6-methyl-5-[(2E, 6E)-3,7,11-trimethyl-2,6,10-dodecatrienyl]benzaldehyde (Scutigeral); 6,7-Deepoxy-6,7-didehydro-5-deoxy-21-dephenyl-21-(phenylmethyl)-20-(4-hydroxybenzeneacetate)daphnetoxin (Tinyatoxin); capsaicin synthetics; capsaicin derivatives; botulinum toxin; anti-convulsants; anesthetics; analgesics; opioids; cannabinoids; N-[2-(4-Chlorophenyl)ethyl]-1,3,4,5-tetrahydro-7,8-dihydroxy-2H-2-benzazepine-2-carbothioamide (Capsazepine); [N-(4-Hydroxy-3-methoxyphenyl)methyl]-5Z,8Z,11Z,14Z-eicosatetraenamide] (Arvanil); N-(3-Methoxyphenyl)-4-chlorocinnamide (SB-366791); 5'-iodoresiniferatoxin; steroids; nonsteroidal anti-inflammatory compounds; COX inhibitors; modulators of TNF-alpha or IL-1 cytokines or receptors; NFkB modulators; minocyclin, fluorocitrate, antioxidants, free radical chelators, and any combination thereof. These therapeutic compounds, formulations, and the methods of use for treatment of discogenic pain are described in details in an co-pending U.S. patent application Ser. No. 11/414,689 entitled Biological Removal Of Vascular And/Or Neuronal Extensions From A Degenerating Disc, filed on Apr. 28, 2006, which is incorporated into the instant disclosure by reference in its entirety.

All patent and non-patent publications cited in this disclosure are incorporated herein in to the extent as if each of those patent and non-patent publications was incorporated herein by reference in its entirety. Further, even though the invention herein has been described with reference to particular examples and embodiments, it is to be understood that these examples and embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

The invention claimed is:

1. A kit for diagnosing the location of a pain generator in a patient or an activity of a pain generator in the patient, the pain generator created by an axial pain condition and the pain generator being present in a target spinal disc or in an area adjacent to a target spinal disc, the axial pain condition being with or without radiculopathy, the kit comprising:
   a parenteral composition comprising:
      a purified pain marker or a purified marker of degeneration; and
      an activator;

wherein the parenteral composition becomes activated when the purified pain marker or the purified marker of degeneration and the activator come into proximity of the pain generator;

wherein the purified pain marker or purified marker of degeneration is associated with a radioisotope label or associated with a fluorochrome label;

wherein the purified pain marker or purified marker of degeneration is located in a polymer depot;

wherein the parenteral composition is provided in a visualizable amount, wherein the visualizable amount is an amount sufficient to be visualized by one of radiography, MRI, PET, SPECT, CT or fluoroscopy when the parenteral composition becomes activated; and wherein the parenteral composition is adapted to allow visualization of the amount of the pain generator or visualization of the activity of the pain generator when the parenteral composition is activated; and means for comparing the amount of the pain generator or for comparing the activity of the pain generator in the target spinal disc or the area adjacent to the target spinal disc with an amount of the pain generator or an activity of the pain generator in a non-target spinal disc or an area adjacent to a non-target spinal disc by allowing visualization of the amount of the parenteral composition which was activated and comparing that amount with the amount of parenteral composition activated at the non-target spinal disc or the area adjacent to the non-target spinal disc; and a detector configured to be inserted into the target spinal disc or the area adjacent to the target spinal disc, the detector having anchors and a sensing area, the sensing area configured to contact and to allow visualization of the parenteral composition, when activated.

2. The kit of claim 1, wherein the kit contains a set of instructions on how to administer the parenteral composition.

3. The kit of claim 1 further comprising an extraction device operable to extract a sample containing tissue from the target disc or the area adjacent to the target disc.

4. The kit of claim 3 wherein the extraction device is a needle having a diameter of 18 G or less and wherein the extraction device is capable of retrieving a sample of up to about 1000 µl.

5. The kit of claim 1 wherein the purified pain marker or the purified marker of degeneration is selected from a group consisting of markers of neuronal, immune, vascular and matrix elements, and any combination thereof.

6. The kit of claim 5 wherein the purified pain marker or the purified marker of degeneration is selected from a group consisting of the markers of the neuronal elements.

7. The kit of claim 6, wherein the purified pain marker or the purified marker of degeneration can label a molecule released by the neuronal elements.

8. The kit of claim 6, wherein the purified pain marker or the purified marker of degeneration is capable of binding to a neuronal receptor.

9. The kit of claim 8 wherein the neuronal receptor is an opioid receptor.

10. The kit of claim 8, wherein the neuronal receptor is a sigma opioid receptor.

11. The kit of claim 5, wherein the purified pain marker or the purified marker of degeneration is selected from a group consisting of markers of vascular elements.

12. The kit of claim 11, wherein the purified pain marker or the purified marker of degeneration can label an angiogenic agent.

13. The kit of claim 11, wherein the purified pain marker or the purified marker of degeneration can label a molecule released by the vascular elements.

14. The kit of claim 5, wherein the purified pain marker or the purified marker of degeneration is selected from a group consisting of markers of immune elements.

15. The kit of claim 14, wherein the purified pain marker or the purified marker of degeneration can label a pro-inflammatory agent.

16. The kit of claim 15, wherein the immune elements are selected from a group consisting of inflammatory-linked cytokines.

17. The kit of claim 5, wherein the purified pain marker or the purified marker of degeneration is selected from a group consisting of markers of matrix elements.

18. The kit of claim 1, wherein the purified pain marker or the purified marker of degeneration can label an extracellular component.

19. The kit of claim 1, wherein the parenteral composition is capable of being administered by a method selected from a group consisting of an intravenous administration, an intramuscular administration, an intrathecal administration, a subcutaneous administration, an epidural administration, an intra-discal administration, a direct application onto or adjacent to the target spinal disc, and any combinations thereof.

20. The kit of claim 19, wherein the activator is capable of being administered by the direct application onto or adjacent to the target spinal disc.

21. The kit of claim 1, wherein the polymer depot is biodegradable.

* * * * *

UNITED STATES PATENT AND TRADEMARK OFFICE
CERTIFICATE OF CORRECTION

PATENT NO. : 8,333,697 B2
APPLICATION NO. : 11/449464
DATED : December 18, 2012
INVENTOR(S) : McKay et al.

It is certified that error appears in the above-identified patent and that said Letters Patent is hereby corrected as shown below:

In Column 3, Lines 39-40, delete "proteglycans," and insert -- proteoglycans, --, therefor.

In Column 4, Line 2, delete "serotonine," and insert -- serotonin, --, therefor.

In Column 4, Line 3, delete "$K^{+Ca2+}$," and insert -- $K^+, Ca^{2+}$, --, therefor.

In Column 9, Line 55, delete "proteglycans," and insert -- proteoglycans, --, therefor.

In Column 10, Line 18, delete "serotonine," and insert -- serotonin, --, therefor.

In Column 10, Line 21, delete "serotonine," and insert -- serotonin, --, therefor.

In Column 10, Line 62, delete "elementss" and insert -- elements --, therefor.

In Column 11, Line 34, delete "serotonine," and insert -- serotonin, --, therefor.

In Column 15, Lines 32-33, delete "phycoerythryn," and insert -- phycoerythrin, --, therefor.

In Column 15, Line 33, delete "o-phtaldehyde," and insert -- o-phthalaldehyde, --, therefor.

Signed and Sealed this
Twenty-ninth Day of January, 2013

David J. Kappos
*Director of the United States Patent and Trademark Office*